United States Patent [19]

Stuns et al.

[11] Patent Number: 5,631,418
[45] Date of Patent: *May 20, 1997

[54] ELECTRICALLY DETECTED IMPEDANCE DETECTOR FOR THE MEASUREMENT OF PHYSICAL QUANTITIES, IN PARTICULAR OF TEMPERATURE OR HUMIDITY, AND PROCESS FOR THE MANUFACTURE OF SAID DETECTORS

[75] Inventors: Ingmar Stuns, Helsinki; Simo Tammela, Espoo; Heikki Turtiainen, Vantaa; Jorma Ponkala, Ylönkylä, all of Finland

[73] Assignee: Vaisala Oy, Vantaa, Finland

[*] Notice: The term of this patent shall not extend beyond the expiration date of Pat. No. 5,483,414.

[21] Appl. No.: 312,886

[22] Filed: Sep. 27, 1994

[30] Foreign Application Priority Data

Sep. 29, 1993 [FI] Finland ................. 934268

[51] Int. Cl.$^6$ ............ H01G 7/00; H01G 5/01; G01K 7/04; G01D 21/02
[52] U.S. Cl. ............ 73/335.05; 73/29.01; 338/35
[58] Field of Search .......... 73/335.02, 335.03, 73/335.04, 335.05, 335.12, 29.01, 29.05; 338/35; 340/605

[56] References Cited

U.S. PATENT DOCUMENTS

| | | | |
|---|---|---|---|
| 2,106,744 | 3/1938 | Hood et al. | 106/36.1 |
| 2,285,421 | 6/1942 | Dunmore | 177/351 |
| 2,295,570 | 12/1942 | Dunmore | 201/63 |
| 2,315,329 | 3/1943 | Hood et al. | 338/35 |
| 2,381,299 | 3/1945 | McCulloch | 201/76 |
| 2,510,018 | 6/1950 | Gillingham | 201/63 |
| 3,168,829 | 2/1965 | Nelson | 73/336.5 |
| 3,295,088 | 12/1966 | Smith | 338/35 |
| 3,299,387 | 1/1967 | Sanford | 338/35 |
| 3,350,941 | 11/1967 | Misevich et al. | 73/336.5 |
| 3,443,293 | 5/1969 | Masujima | 29/25.42 |
| 3,458,845 | 7/1969 | Thoma | 338/35 |
| 3,559,456 | 2/1971 | Lomker et al. | 73/29.05 |
| 3,683,243 | 8/1972 | Rockliff | 73/335.04 |
| 3,935,742 | 2/1976 | Rybak | 73/336.5 |
| 4,083,030 | 4/1978 | Gröninger | 338/35 |

(List continued on next page.)

FOREIGN PATENT DOCUMENTS

| | | | |
|---|---|---|---|
| 0564428 | 10/1993 | European Pat. Off. | |
| 59-133452A | 7/1984 | Japan | 73/335.03 |
| 872042 | 9/1957 | United Kingdom | |
| 2234820 | 8/1990 | United Kingdom | |

OTHER PUBLICATIONS

"Multifunctional Ceramic Sensors: Humidity–Gas Sensor and Temperature–Humidity Sensor", by Tsuneharu Nitta, IEEE Transactions on Electron Devices, vol. ED29, No. 1, Jan. 1982.

"A Thin Film Polyimide Based Capacitive Type Relative Humidity Sensor", by Takaaki Kuroiwa et al, Sensors and Actuators B, 13–14 (1993) 89–91.

FI933702(English translation).

Primary Examiner—Hezron E. Williams
Assistant Examiner—Jay L. Politzer
Attorney, Agent, or Firm—Jones & Askew

[57] ABSTRACT

Electrical impedance detector for measurement of physical quantifies, in particular of temperature or humidity. The detector comprises conductor electrodes (10a, 10b; 10A, 10W), between which the electrical impedance ($C_M$) that represents the physical quantity to be measured is measured. Between the conductor electrodes (10a, 10b;10A, 10W) there is an active material (11;11P) whose impedance properties are a function of the physical quantity to be measured. The detector is composed of pieces cut-off out of a continuous detector filament (20; 20H;20K), which detector filament (20;20H;20K) comprises a conductive electrode wire or an assembly of electrode wires (10a, 10b; 10A, 10W), on/between which there is an active material (11;11P) whose impedance properties are a function of the physical quantity to be measured. Further, a novel process is described for the manufacture of said detectors.

10 Claims, 4 Drawing Sheets

U.S. PATENT DOCUMENTS

| | | | |
|---|---|---|---|
| 4,319,485 | 3/1982 | Terada et al. | 73/336 |
| 4,347,550 | 8/1982 | Rockliff | 361/286 |
| 4,481,813 | 11/1984 | Tanei et al. | 73/336.5 |
| 4,553,432 | 11/1985 | Barlian et al. | 73/335.05 |
| 4,858,063 | 8/1989 | Laue et al. | 361/286 |
| 5,028,906 | 7/1991 | Moriya et al. | 73/335.05 |

$S_1$ ↓ CRYSTALLISATION (800°C, 30 min)
GLASS -> GLASS-CERAMIC $S_2$ ↓ COATING BY GLASS OR GLASS PASTE

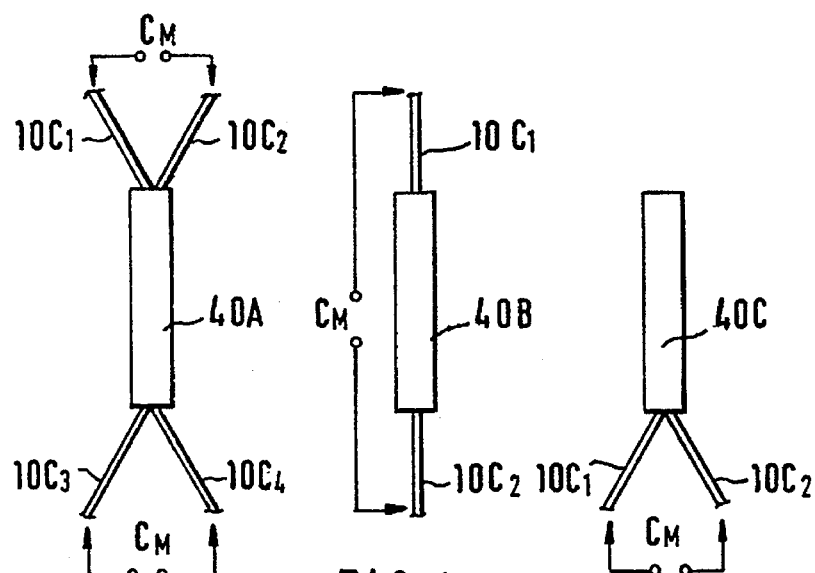
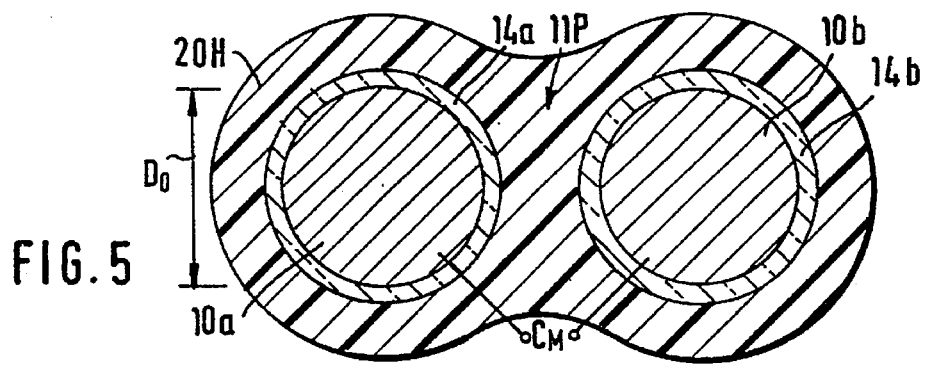
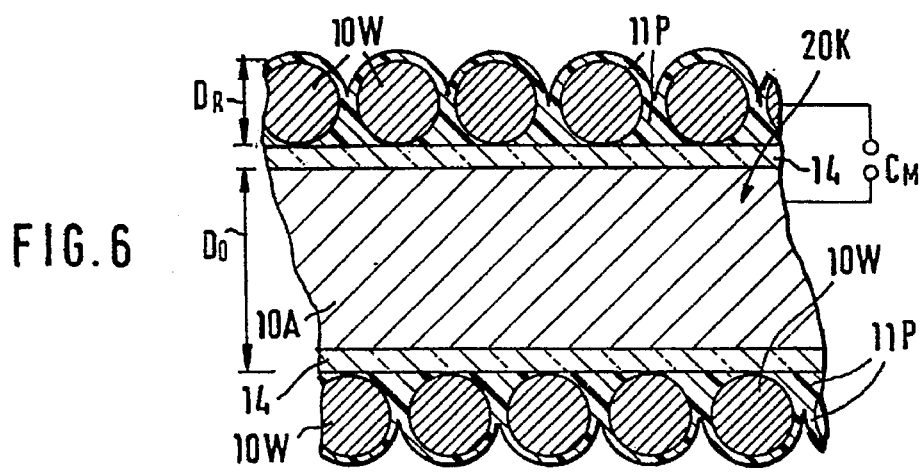

ELECTRICALLY DETECTED IMPEDANCE DETECTOR FOR THE MEASUREMENT OF PHYSICAL QUANTITIES, IN PARTICULAR OF TEMPERATURE OR HUMIDITY, AND PROCESS FOR THE MANUFACTURE OF SAID DETECTORS

FIELD OF INVENTION

The invention concerns an electrical impedance detector for measurement of physical quantities, in particular of temperature or humidity, which detector comprises conductor electrodes, between which the electrical impedance that represents the physical quantity to be measured is measured, and between which electrodes there is an active material whose impedance properties are a function of the physical quantity to be measured.

Further, the invention concerns a process for manufacture of electrical impedance detectors, said detector being intended for measurement of physical quantities, in particular of temperature or relative humidity.

BACKGROUND OF INVENTION

In a number of applications, high speed, small size, and low radiation error are required from measurement detectors, in particular from detectors intended for measurement of temperature or relative humidity. Said requirements are particularly strict, e.g., in detectors of radiosondes.

As is known in prior art, for example, as temperature detectors of radiosondes, as a rule, capacitive detectors are used, whose active material is a ceramic whose dielectricity is dependent on the temperature. The prior-art glass-ceramic temperature detectors are, however, of relatively large size, and therefore their speed and radiation error would require some improvement. The radiation error produced by solar radiation has been the most important problem in the temperature measurement by radiosondes with the use of prior-art temperature detectors.

Besides capacitive detectors, in radiosondes and equivalent, resistive temperature detectors and thermoelements have also been used.

In the prior art, capacitive humidity detectors are known in whose capacitance the dielectric material used is a polymer, a ceramic, or a glass-ceramic whose dielectric constant is a function of the humidity absorbed by it. The speed and corresponding properties of these detectors also require development, in particular in view of radiosonde applications.

As regards the prior-art electrically detected temperature and humidity detectors, reference is made, e.g., to the U.S. Pat. Nos. 3,168,829 and 3,350,941 as well as to the applicant's FI Patent No. 48,229, in which latter FI patent a capacitive humidity detector is described in which the dielectric insulating material is a polymer film whose permittivity is a function of the amount of water absorbed by the polymer film.

The substantial construction of the humidity detector described in said FI patent is a thin plate, onto whose face a structure sensitive to humidity has been processed. A drawback in this prior-art construction is the scattering of the permeability to water of the surface electrode and the resulting scattering of speed of the detector. Further, the size of the construction is quite large, which produces a radiation error especially in radiosonde operation, because the face subjected to solar radiation is considerable and its ventilation is relatively poor. Since, in said prior-art detector, the active face is straight, water tends to remain on this face as drops.

The processes of manufacture of the prior-art impedance detectors and equivalent have been complicated, frequently poorly suitable for automation and poorly suitable for continuous processes of manufacture. The prior-art processes of manufacture of said detectors have been demanding and consisted of a number of steps, in particular in an attempt to obtain a detector as rapid and accurate as possible, which usually requires very small size and precise dimensioning from the constructions and good control of the various parameters in the processes of manufacture.

With respect to the most recent development work carried out by the applicant, related to and closely connected with the present invention, reference is made to the following FI Patent Applications: No. 921449 (filed Apr. 1, 1992), No. 933701 (filed Aug. 23, 1993) and No. 933702 (filed Aug. 23, 1993). The constructions and methods described in said applications can, where applicable, also be used in combination with the present invention.

The object of the present invention is further development both of the constructions and of the processes of manufacture of the prior-art humidity detectors so as to avoid the drawbacks mentioned above and to achieve the objectives stated above and those that will come out later.

The process and the detector construction described in the applicant's FI Patent Application No. 921449 (filed Apr. 1, 1992, became public Oct. 4, 1993) (equivalent to U.S. Pat. Appl. Ser. No. 08/040,129 and to EP Application 93 850 046.9) are most closely related to the present invention. In said FI patent application, an electrical impedance detector is described, in which the active material between its electrodes is expressly a very thin thread-like glass or glass-ceramic fibre prepared by the glass-drawing technique. Said fibre is a glass-ceramic fibre whose drawing into fibreglass thread has been carried out in glassy form whereas the crystallization into the glass-ceramic form has been carried out in a heat treatment. In the glass-ceramic material the active constituent is crystalline barium-strontium titanate $Ba_xSr_{1-x}TiO_3$ or crystalline lead-strontium titanate $Pb_xSr_{1-x}TiO_3$, wherein x is in the range of 0 ... 1, and which is placed in a glass matrix. The cross-sectional shape of the detector thread is substantially circular, and its diameter is of an order of 25 ... 500 µm.

The construction of the detector described in said FI Pat. Appl. 921449 is preferably coaxial, comprising a solid central electrode wire or an equivalent hollow electrode wire and a glass or glass-ceramic layer placed around said electrode, on which layer there is a hermetic glass layer, and on it an electrode layer and/or electrode fibres which have been applied in a separate step. Said detector may be composed of two detector fibre threads, which are joined together by means of a parallel joint, e.g. an adhesive joint, over a certain length. Further, in said FI patent application, a method is described for the manufacture of electrical impedance detectors, which method comprises a combination of the following steps:

a continuous detector-fibre thread of substantially circular section is manufactured by means of a glass-drawing technique in itself known out of a molten glass mix which has been alloyed with an additive or with additives that provide (s) the active material of the detector with suitable electrical properties; the detector-fibre thread is crystallized by means of heat treatment into a glass-ceramic form or its material is chosen or otherwise treated so that an active detector material is produced whose capacitance and/or resistance depend on the temperature or, in particular cases, on the mount of water absorbed by the active material; and, for individual detectors, said detector-fibre thread is cut-off into suitable pieces of detector-fibre thread, to which terminals are connected, and/or to whose electrodes, which have been provided at the thread-drawing stage, terminals are coupled or connected, between which terminals the impedance of the detector can be measured.

In the process of said FI Pat. Appl. 921449 described above, the drawing of the detector fibre thread is carried out by using a double-crucible process known in itself from the manufacture of optical fibres, in which process, in the inner crucible, molten core glass is used, to which strontium, barium and titanium oxide and/or an equivalent other additive have been added, and in the outer crucible molten glass material is used, such as aluminosilicate glass, from which a tubular hermetic outer layer is obtained onto the detector fibre thread. In the process of said FI patent application, into the molten detector fibre, an electrode wire is fed, or the inner electrode is passed into a glass-tube blank, which are then together drawn into a detector fibre thread, or first a hollow detector fibre thread is prepared and its interior is metallized afterwards. In said process, the detector fibre thread is coated with a conductive electrode layer by passing the fibre thread through a crucible with a hole in its bottom and through an oven, said crucible containing conductive paste as the coating paste. Onto the fibre thread, conductor patterns are applied by vapour-deposition or by a photolithographic method. In the process, from the continuous detector fibre thread, pieces of about 1 ... 5 cm are cut off, which pieces are joined together side by side by means of a longitudinal joint, or detector wires are attached to both sides of a piece of detector fibre thread. In the process of said FI application, the electrode wire does not operate as a carrier or drawing wire in the process of manufacture, said carrier or drawing wire being expressly a fibreglass thread.

SUMMARY OF INVENTION

The object of the present invention is further development both of the constructions and of the processes of manufacture of the prior-art impedance detectors so as to avoid the drawbacks mentioned above and to achieve the objectives stated above and those that will come out later.

A particular object of the present invention is further development of the inventive ideas described in said FI Pat. Appl. 921449, so that both the detector construction and the process for its manufacture can be simplified further and that their range of application can be extended also to detectors other than temperature detectors, in particular to detectors used for measurement of relative humidity.

In view of achieving the objectives stated above and those that will come out later, the electrical impedance detector in accordance with the invention is mainly characterized in that the detector is composed of pieces cut-off out of a continuous detector filament, which detector filament comprises a conductive electrode wire or an assembly of electrode wires, on or between which there is an active material whose impedance properties are a function of the physical quantity to be measured.

On the other hand, the process of manufacture of the detector in accordance with the invention is mainly characterized in that the process comprises a combination of the following steps:

(a) detector filament is manufactured as a continuous drawing process by using a conductive electrode wire or assembly of electrode wires as a carrier wire and as drawing means, (b) in a continuous filament process, said electrode wire or assembly of electrode wires is coated with an active material whose impedance properties are a function of the physical quantity to be measured, and (c) out of the continuous detector filament obtained from the steps (a) and (b), pieces of a length suitable for the purpose of use are cut off, the electrode wire or wires being uncovered from one or both ends of said filament pieces so as to form electrical contact points for the impedance detector.

In this connection, it should be emphasized that, in the coating step (b) defined above, coating does not necessarily mean that the active material surrounds the electrode wire or wires completely, even though that is also possible.

In the invention, the electrode wire, preferably a pair of electrode wires or a corresponding assembly of electrode wires, operates in the process of manufacture as the drawing and carrier wire, which receives the tensile strains necessary in the process of manufacture and which electrode wire or assembly of wires gives the finished detector a substantial proportion, preferably the principal proportion, of its mechanical strength. In the process of the invention, the other layers and parts of the detector are processed and made to adhere expressly in connection with the electrode wire or assembly of electrode wires, and not in connection with the fibreglass thread, which is the case in the process and detector of said FI Pat. Appl. 921449, for which reason the process becomes simpler and less susceptible of disturbance, and the detector construction becomes simpler, in particular because the electrode wires constitute preferably both of the electrical electrodes for the detector, between which electrodes the detector impedance can be measured, and the electrode or electrodes need not be manufactured in separate steps. When a pair of electrode wires or a higher number of electrode wires are used, in the coating process the active material is made to adhere to the electrode wires, and the electrode wires are connected with each other by means of the active material even if the active material does not necessarily enclose the electrode wires completely, as is shown, e.g., in the following FIGS. 3A, 3B and 3C.

The principal steps in a preferred embodiment of the process of the invention are the following: preparation of the glass material, drawing of a filament pair or of several filaments, crystallization of the glass, coating to form protection against moisture, and cutting off of the filament as well as removal of the glass-ceramic from the ends of the detector so as to uncover the electrode wires to constitute electrical contact wires for the detector. The sequence of the steps is not necessarily that given above, but, for example, the cutting-off can already be carried out before crystallization or between the crystallization and the moisture-protection coating. So also, the protection against moisture can be applied to a detector that has already been cut off and attached to a support construction. In the step of making of the glass material, the starting materials are melted in a crucible and cast out of a suitable material. The glass is cooled sufficiently rapidly, so that it is not crystallized but remains in a glassy form. The cast glass pieces are placed into a crucible provided with a hole in the bottom, which is placed in an oven. The wires to be coated are drawn through the crucible and further to a drawing device placed underneath the oven. The wires are made, e.g., of platinum, and their thickness is typically ~50 μm.

The following crystallization is a two-stage heat treatment, for example, first 1 h at 500° C. and thereupon 0.5 h at 800° C. In the crystallization, the glass material is converted to a glass-ceramic, and strontium and barium titanate crystals are formed in it. At the same time, the dielectric constant of the glass material is increased and becomes highly dependent on the temperature. The next step of coating with a protection against moisture takes place in a way similar to the drawing of the filament pair by means of a crucible with a hole in its bottom. As the coating material, for example, a glass is used which has substantially the same thermal expansion coefficient as that of the glass-ceramic that is used and whose softening point is below the temperature of crystallization of the glass-ceramic.

Out of the coated finished detector filament, detector pieces of suitable length are cut off, the moisture protection and the glass-ceramic being removed from one or both ends of said detector pieces, e.g., by etching by means of hydrofluoric acid. From the uncovered conductor wires the detector can be attached to a suitable support construction by soldering or by means of an electrically conductive adhesive. In a way similar to a filament pair, it is, of course, also possible to coat a single wire, such as a platinum wire, with a glass-ceramic or equivalent and to make different coaxial detector constructions.

The detector filament can also be made by using glass paste. Also in this case, a crucible with a hole in the bottom can be used for coating. It is a difference as compared with the exemplifying embodiment described above that the crucible contains glass paste and is at the room temperature. The paste is prepared in a way similar to a conventional thick-film paste out of a glass whose thermal expansion coefficient is close to the thermal expansion coefficient of platinum. After the crucible, the filament is passed through a tubular oven, in which the paste is sintered by using the temperature profile required by the paste concerned. Likewise, the moisture protection of a filament pair can be prepared by means of glass paste. In such a case, the sintering temperature must be sufficiently low in order that crystallization of the glass-ceramic should not take place during the sintering.

The moisture protection can also be applied at a later stage when the detector has already been attached to its support construction, by using a suitable coating, such as glass, diamond-like coatings, metallization, polymer coatings, etc. or combinations of same.

Further, the whole detector in accordance with the invention can be coated with a grounded metal layer penetrable by moisture, in which case a capacitive error arising from possible water drops is avoided, and at the same time also other errors arising from irregularities in the surface are avoided.

By means of the method of the invention, the detector filament can be manufactured relatively easily as a continuous process free from disturbance. The means of manufacture are simple and inexpensive.

In the following, the invention will be described in detail with reference to some exemplifying embodiments of the invention illustrated in the figures in the accompanying drawing, the invention being by no means strictly confined to the details of said embodiments.

BRIEF DESCRIPTION OF DRAWINGS

FIG. 3B is, at the same time, a sectional view B—B in FIG. 2.

FIG. 3B is, at the same time, a sectional view taken along the line C—C in FIG. 2.

FIGS. 4A, 4B and 4C illustrate different embodiments of a finished detector in accordance with the invention.

FIG. 5 is a sectional view of a preferred humidity detector in accordance with the invention.

FIG. 6 is a central axial sectional view through the detector filament of a second preferred humidity detector in accordance with the invention.

DESCRIPTION OF PREFERRED EMBODIMENTS

Figure 1:
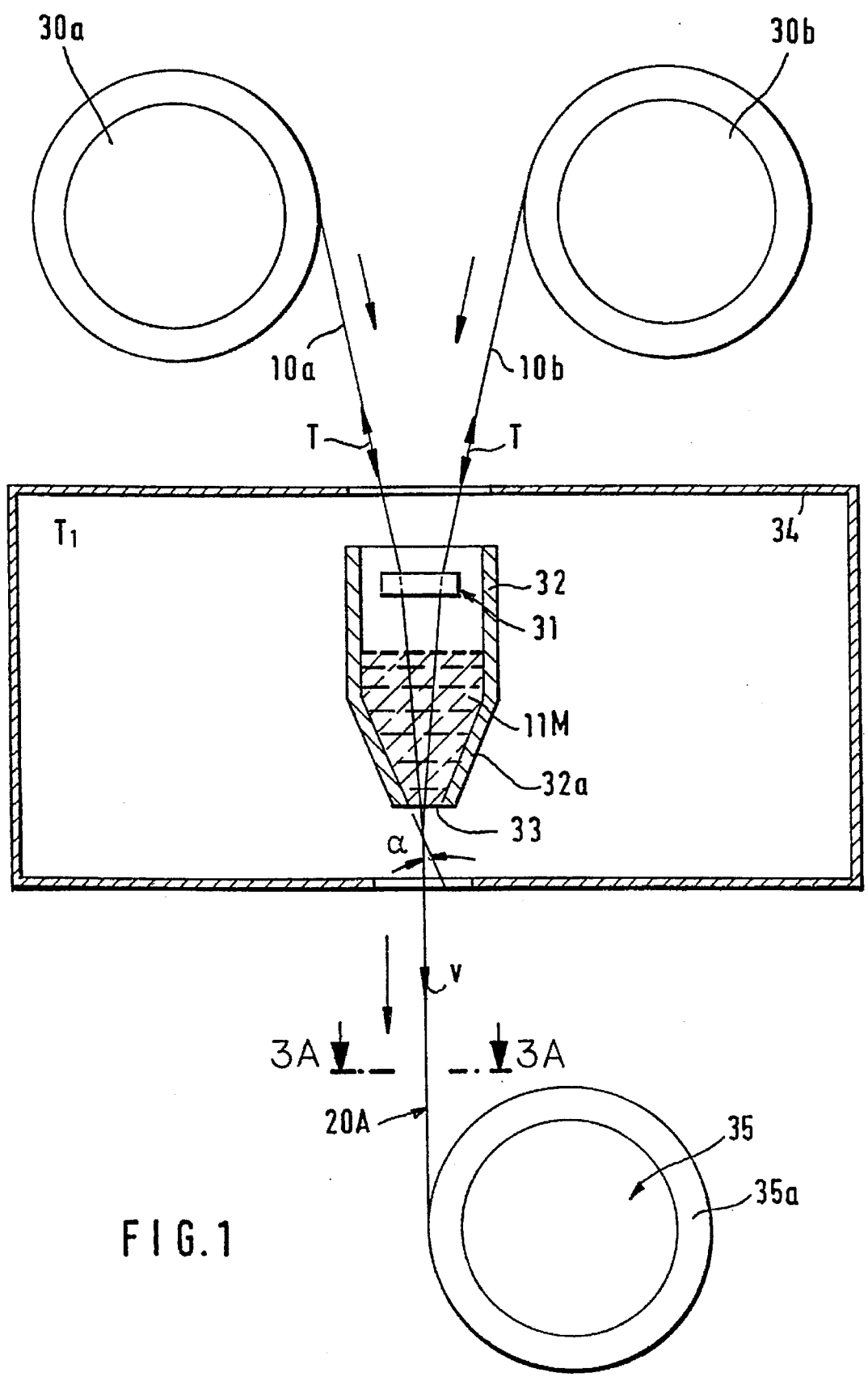
FIG. 1 is a schematic illustration of a process step in accordance with the invention in which a pair of electrode wires is drawn from a pair of upper reels onto a lower reel through a wire guide and through a crucible placed in an oven.

According to FIG. 1, the manufacture of the detector filament takes place by using a pair of electrode wires $10a$ and $10b$ as the carrier wire and the drawing means in the continuous filament process, which wires are drawn from the starting reels $30a$ and $30b$ through the crucible 32 placed in an oven 34. The glass material 11M placed in the crucible 32 is prepared as follows. The starting materials of the glass material 11M are melted in a platinum crucible and east into a mold made of a suitable material, such as copper. The molten glass can also be poured into a vessel fried with water. It is essential that the glass is cooled sufficiently rapidly so that it is not crystallized but remains in the glassy form. The cast pieces of glass 11M are cleaned and placed into a platinum crucible 32 with a hole in its bottom, which crucible is placed in an oven 34. For the oven, a tubular or annular oven is suitable, of a sort that is used, e.g., in the drawing of optical fibre. The electrode wires $10a$ and $10b$ to be coated are drawn from two starting reels $30a$ and $30b$ placed above the oven 34 through the wire guide 31 and through the crucible 32 and further to the reeling and drawing device 35 placed below the oven 34. The electrode wires $10a$, $10b$ are, e.g., of platinum, and their diameter $D_0$ is typically $D_0 \approx 50$ μm.

Figure 3A:
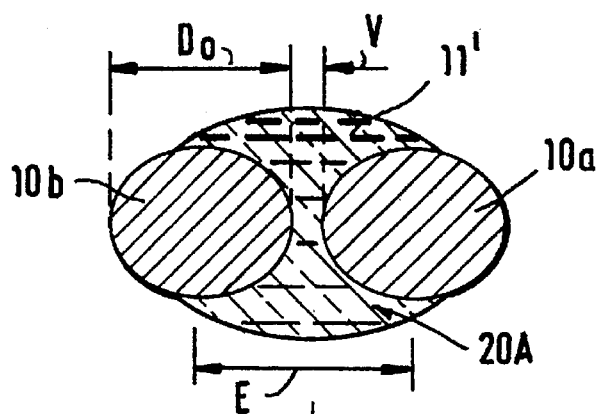
FIG. 3A is a sectional view of a detector-filament blank taken along the line A—A in FIG. 1.

The oven 34 shown in FIG. 1 is heated to such a temperature $T_1$ that the glass material 11M is softened appropriately, and the electrode wires $10a$, $10b$ are drawn by means of the reeling and drawing device 35 so that, when passing through the crucible 32, they are combined and partly coated with molten glass 11' (FIG. 3A). By means of the wire guide 31 and of the drawing tension T of the wires $10a$, $10b$, the process can be controlled so that the wires $10a$, $10b$ do not reach contact with one another but that a thin layer of glass 11' remains between them, which layer interconnects the electrode wires $10a$, $10b$. By regulating the temperature $T_1$ and the drawing speed v, it is possible to affect the thickness of the glass layer 11'. By means of suitable selection of the parameters $T, v, D_0$, a filament-pair blank 20A is produced (FIG. 3A) in which glass 11' remains between the filaments $10a$, $10b$ only. In such a case, the detector diameter and, at the same time, its radiation error and response time can be minimized. At this stage, it is essential that the coated filament blank 20A cools sufficiently rapidly after the oven 34 so that it is not crystallized.

In the way described above, by means of the device and the process step as illustrated in FIG. 1, a detector-filament blank 20A of a section similar to that shown in FIG. 3A has been produced, which is reeled onto the drawing reel 35. After this, the crystallization stage follows, which is denoted with $S_1$ in FIGS. 3A–3B.

Figure 3B:
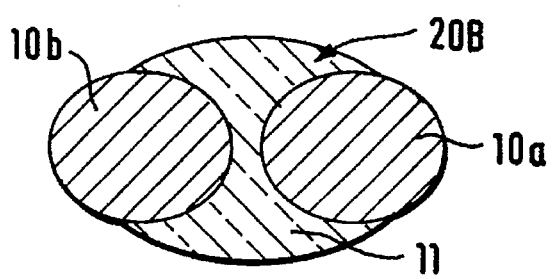
FIG. 3B shows a corresponding detector-filament blank after the crystallization stage.

The next step is crystallization. This crystallization step $S_1$ consists of a two-stage heat treatment, for example, first ~1 h at 500° C. and then ~0.5 h at 800° C. At this crystallization stage, the glass layer 11' in the blank 20A is convened to a glass-ceramic layer 11, and into it strontium and barium titanate crystals or equivalent are formed. At the same time, the permittivity $\epsilon$ of the glass-ceramic layer 11 is increased and becomes highly dependent on the temperature, $\epsilon=f(T)$. In this way, the detector-filament blank 20B as shown in FIG. 3B is obtained. The temperatures and crystallization times that are used act upon the sorts of crystals that are formed in the glass as well as upon the amount and size of the crystals, and thereby upon the dielectric properties of the glass-ceramic layer 11 that is formed. The heat treatment takes place, e.g., so that the pair-filament blank 20A is drawn through a tubular oven whose temperature profile has been regulated appropriately.

The diameter $D_0$ of the electrode wires 10a and 10b is typically $D_0 \approx 5$ μm ... 500 μm, and the distance E between the electrode wires 10a and 10b is typically $E \approx 6$ μm ... 1000 μm. The shortest distance V between the detector wires 10a and 10b is $V \approx 1$ μm ... 500 μm.

In the following, based on FIG. 1, an exemplifying test embodiment of the invention that has been carried out in practice is described: The equipment of manufacture of the detector filament consisted of a device 30a, 30b for the feed of platinum wires 10a, 10b, of a platinum crucible 32 placed in an oven 34, and of a device 35 for drawing and reeling of the detector filament. The diameter D of the platinum wires 10a, 10b was $D=50$ μm. The drawing tension T of the wires was $T=0.3 \ldots 15$ cN (centi Newton). From the reels 30a, 30b the wires 10a, 10b passed side by side through the platinum crucible 32 placed in the drawing oven, which crucible contained about 1 gram of glass 11M. The glass 11M drawing temperatures used were $T_1=1020° \ldots 1100°$ C.

The temperature at the tip 33 of the crucible 32 was about 100° C. lower than the maximum temperature. The opening angle of the bottom cone in the nozzle part 32a was $2\alpha=20° \ldots 45°$, and the diameter of the hole 33 in the crucible was 500 ... 900 μm. The drawing speeds v that were used were $v=2 \ldots 6$ cm/s. Above the crucible 32, about 100 mm above the glass melt 11M, there was a wire guide 31 made of platinum and keeping the wires separate from one another. By means of this guide, the wires 10a, 10b could be made to run separately through the upper orifice of the crucible 32. As the reeling and drawing device 35, an equipment of the capstan type was used. The glazed filament was drawn by means of a drawing wheel 35a of a diameter of 320 mm. By means of the test draws carried out by means of the test equipment described above, blanks 20A of a pair-filament glass-ceramic temperature detector were produced, whose lengths varied in the range of 2 ... 5 m. The shortest gap between the wires 10a, 10b in the blank 20A was $V=5 \ldots 10$ μm, and the cross-sectional form became elliptic, while the maximum diameter was $D_1 \approx 150$ μm and while the capacitance per unit of length of the filament was of an order of 1 pF/mm.

From the steps described above, a detector-filament blank 20B as shown in FIG. 3B is obtained, in which the insulating material 11 between the electrode wires 10a and 10b is in crystallized form. By means of the device shown in FIG. 2, the process step $S_2$ between FIGS. 3B and 3C is carried out. This filament blank 20B is wound onto the starting reel 36a shown in FIG. 2, from which reel the filament blank 20B is drawn through the crucible 37. In the crucible 37, whose bottom 38 is provided with a hole, the coating material consists of molten coating glass 12M, which has substantially the same thermal expansion coefficient as that of the glass-ceramic in the insulation material 11 and whose softening point is below the crystallization point of the glass-ceramic. After the perforated bottom 38 of the crucible 37, the detector-filament blank is passed through the drying oven 39, whose temperature is $T_2 \approx 150°$ C. After the oven 39, the finished detector filament 20 has a section similar to that shown in FIG. 3C, so that the electrode wires 10a and 10b and the active glass-ceramic material 11 between them are surrounded by an insulating glass layer 12, onto which, if necessary, it is possible to apply a further conductive protection and/or insulation layer 13 in the same stage or in a different stage. The finished detector filament 20 is reeled onto the arrival reel 36b shown in FIG. 2. In FIG. 3C, the detector filament 20 is of elliptic section, and its longer diameter $D_1 \approx 150$ μm, when $D_0 \approx 50$ μm and $V \approx 10$ μm. The capacitance $C_M$ to be measured, which depends on the temperature of the detector, is detected between the detector wires 10a and 10b.

From the stage described above, a complete detector filament 20 is obtained, which is cut off into pieces of suitable length, e.g. when temperature detectors for radiosondes are manufactured, into pieces of a length of about 3 cm. After this, from one end or both ends of the pieces of detector filament, the layers 12, 13 are removed and between the electrode wires 10a, 10b the layer 11 is removed, for example, by etching with hydrofluoric acid. In this way, finished detectors 40A, 40B and 40C are obtained similiar to those shown in FIG. 4. In the detector 40A as shown in FIG. 4A, from both ends of the detector filament, the electrode wires $10C_1$, $10C_2$ and $10C_3$, $10C_4$ have been uncovered. The capacitance $C_M$ proportional to the temperature can be measured either between the electrodes $10C_1$, $10C_2$ or between the electrodes $10C_3$, $10C_4$. According to FIG. 4B, just one detector wire $10C_1$ and $10C_2$ has been uncovered at each end of the piece of detector filament 40B, and the detector capacitance $C_M$ of the detector 40B can be measured between said electrode wires $10C_1$ and $10C_2$. According to FIG. 4C, both of the electrode wires $10C_1$ and $10C_2$ have been uncovered at one end of the piece of detector filament 40C only, and the capacitance $C_M$ can be measured between said electrode wires.

Instead of a pair of electrode wires 10a, 10b, in exceptional cases, it is also possible to use more than two electrode wires, which can be connected either in parallel or in series for the purpose of measurement of the impedance proportional to the physical quantity to be measured. In some exceptional cases, it is also possible to use just one electrode wire, and the detector filament is composed of two component filaments coated with an active agent, e.g., by gluing them together or by melting them together in the process of manufacture, as is described in more detail in the FI Pat. Appl. 921449 mentioned above.

In capacitive detectors, the capacitance of the detector filament 20 per unit of length is, as a rule, of the order of 0.1 ... 10 pF/mm, in radiosonde applications preferably of the order of 1 pF/mm. When a pair of detector wires 10a, 10b is used, their diameters $D_0$, which need not necessarily be equal to one another, are, as a rule, chosen in the range of $D_0 \approx 5$ μm ... 500 μm, in radiosonde detectors preferably $D_0 \approx 10$ μm ... 250 μm. The maximum diameter $D_1$ of a finished detector filament 20 is chosen, as a rule, in the range of $D_1 \approx 15$ μm ... 1500 μm, in radiosonde detectors preferably $D_1 \approx 25$ μm ... 750 μm. From the detector filament, pieces of detector filament are cut off, whose length is, as a rule, chosen in the range of 0.5 cm ... 50 cm, in radiosonde detectors preferably in the range of 1 ... 10 cm.

FIG. 5 shows a humidity detector in accordance with the invention, in which the body and the electrodes of the detector 20H consist of two thin metal wires 10a, 10b, for example nickel wires of a diameter of $D_0 \approx 10$μ. The wires 10a and 10b are cleaned and preferably coated with a thin insulating layer 14a and 14b that has a dielectricity as high as possible. After this, both of the wires 10a, 10b are drawn side by side through a container in which there is an active polymer dissolved in a suitable solvent, whereby the wires 10a, 10b are coated by the effect of capillary forces and glued together by means of the active insulating layer 11P. The same capillary forces prevent the wires 10a, 10b from entering into tight contact with one another. After evaporation of the solvent, finished detector filament 20H is obtained. After the wires have been separated, e.g., mechanically from the layer 11P and uncovered from the insulations 14a, 14b, finished humidity detectors are obtained.

Figure 2:
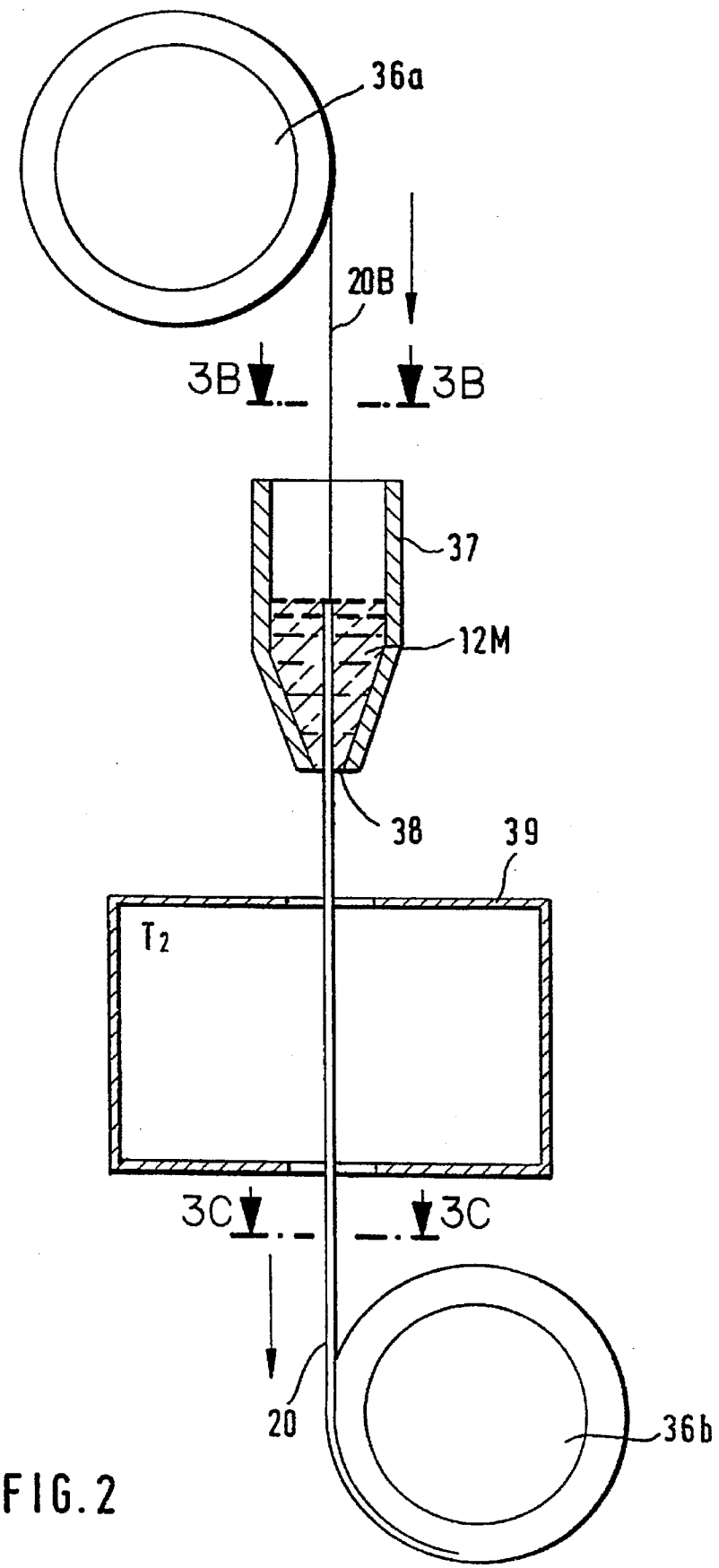
FIG. 2 shows a process step following after the process step as shown in FIG. 1, in which the detector-filament blank is coated with a glass paste and is thereupon dried in an oven as a continuous process running from one reel onto the other.
Figure 3C:
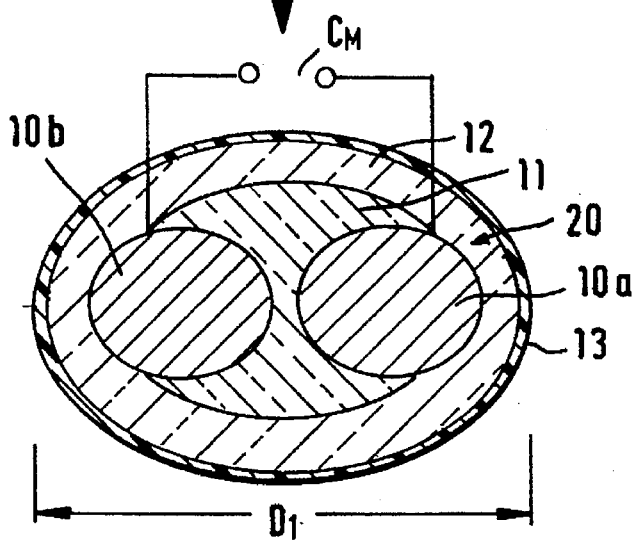
FIG. 3C is a sectional view of a finished detector-filament blank.

If the active material used in FIG. 5, such as a polymer 11P in itself known, can be melted, the wires 10a, 10b can also be drawn through this melt by means of an equipment similar to that shown in FIG. 2. The detector wires 10a, 10b do not have to be of equal thickness as compared with one another.

FIG. 6 is a central axial sectional view in the longitudinal direction of the detector filament of an alternative embodiment of a humidity detector 20K. In the detector as shown in FIG. 6, there is one central electrode wire 10A, whose diameter $D_0$ is typically $D_0 \approx 200$ μm. The cleaned wire 10A is coated with a thin insulating layer 14. Around the insulating layer 14, with a low pitch, a wire is wound side by side that is substantially thinner than the centre wire 10A, the diameter $D_R$ of said wire being $D_R \approx 10$ μm. Said wire assembly 10A, 10W is drawn through a solution that contains active material 11P in a way similar to the steps described above in relation to FIG. 5. In such a case, the active material 11P fills the gaps between the wire windings 10W and coats them so that the material 11P forms the dielectric of the capacitance $C_M$ that can be measured between the electrodes 10A and 10W.

In stead of being humidity detectors, the detectors 20H and 20K shown in FIGS. 5 and 6 may also be, for example, temperature detectors, in which case the permittivity of the insulating material 11P changes, not as a function of humidity but as a function of temperature.

The detectors 20H and 20K as shown in FIGS. 5 and 6, and so also the detectors shown in FIGS. 4, may also be resistive detectors, in which case the resistance of the active insulating material 11;11P is a function of the physical quantity to be measured, such as temperature, humidity, or an equivalent quantity.

Of the detector of FIG. 6, it is also possible to make a modification in which, for example, two wires of substantially equal thickness and coated with an insulation are used, which are wound together with a gentler or steeper spiral form, and said spiral is coated with an active material layer 1ib, for example with a polymer, whose permittivity is a function of humidity if humidity detectors are produced.

In the following, the patent claims will be given, and the various details of the invention may show variation within the scope of the inventive idea defined in said claims and differ from what has been stated above by way of example only.

We claim:

1. Process for manufacturing electrical impedance detectors intended for measurement of physical quantities, in particular of temperature or relative humidity, the process comprising the steps of:

simultaneously drawing at least two conductive electrode wires (10a, 10B) in a continuous process as a carrier wire and a drawing means through an active coating material (11, 11P) whose impedance properties are a function of the physical quantity to be measured, so as to form a continuous detector filament (20, 20H, 20K) in which the electrode wires are joined together by means of the coating material and the coating material remains between the electrode wires;

from the continuous detector filament, cutting off pieces of a length suitable for use as the impedance detectors; and uncovering at least one end of the electrode wires (10a, 10b; 10A, 10W) of the cut-off pieces so as to form electrical contact points for the impedance detectors.

2. Process as claimed in claim 1 for manufacture of a capacitive temperature detector, characterized in that the pair of electrode wires (10a, 10b) or a higher number of electrode wires are drawn from starting reels (30a, 30b) through molten glass material (11M) placed in a crucible (32) so that a detector-filament blank (20A) is formed, in which the electrode wires are joined together by means of glass material (11'), and that said glass material (11') is crystallized by means of heat treatment into glass-ceramic form (11).

3. Process as claimed in claim 2, characterized in that the tensile strain (T) of the electrode wires (10a, 10b), the drawing speed (v), the temperature of the glass mix, and the distribution of the temperature in the crucible and the distance between the electrode wires (10a, 10b) at the top level of the glass mix are chosen so that, during drawing, the electrode wires (10a, 10b) are not short-circuited, but a glass layer of suitable thickness remains between them.

4. Process as claimed by claim 1, characterized in that, from either one or both ends of the pieces of detector filament, the active material layer (11; 11P) and protective layer or layers (12, 13), if any, are removed by etching.

5. Process as claimed in claim 1 for the manufacture of a humidity detector, characterized in that two thin metal wires (10a, 10b) that are provided with an insulating coating, are drawn through an active polymer material (11P) placed in a container, so that said metal wires (10a, 10b) are coated at least partly by the effect of capillary forces and glued together, applying said step of cutting off to the detector filament (20H) obtained in the preceding steps, and uncovering the electrode wires (10a, 10b) mechanically or chemically from one end or both ends of said detectors to constitute connecting wires for the detector.

6. Process as claimed in claim 1, characterized in that one electrode wire is a central wire (10A) coated with an insulating layer (14), another electrode wire is a metal wire (10W) that is substantially thinner than said central wire (10A) and is wound around the central wire in assembly, and that said assembly of wires (10A, 10W) is coated with an active material (11P) so that the impedance to be measured is formed between said detector wires (10A, 10W).

7. Process as claimed in claim 1, characterized in that the diameters $D_0$ of the electrode wires (10a, 10b) are chosen in the range of $D_0 \approx 5$ μm . . . 250 μm, and that the maximum diameter $D_1$ of a finished detector filament (20) is chosen in the range of $D_1 \approx 15$ μm . . . 1500 μm, and that pieces of detector filament from said detector filament (20) are cut off in lengths chosen in the range of 0.5 cm . . . 50 cm.

8. Process as claimed in claim 1 for the manufacture of a humidity detector, characterized in that at least two electrode wires comprise two thin filaments coated with metals and drawn through an active polymer material (11P) placed in a container, so that said filaments are coated at least partly by the effect of capillary forces and joined together by the coating applying said step of cutting off to the detector filament (20H) obtained in the preceding steps, and uncovering the electrode wires (10a, 10b) either mechanically or chemically from either one end or both ends of said detectors to constitute connecting wires for the detector.

9. An electrical impedance detector for measurement of a physical quantity, the detector being cut off from a continuous detector filament (20K) comprising a central electrode wire (10A) surrounded by an electrically insulating layer (14) around which is wound a second electrode (10W) that is substantially thinner than said central electrode wire, the electrodes being surrounded with an active material (11P) whose impedance properties are a function of the physical quantity to be measured.

10. Detector as claimed in claim 9, characterized in that said central electrode wire (10a) gives the detector the primary portion, of its mechanical strength.

* * * * *